US006236049B1

(12) United States Patent
Thomas et al.

(10) Patent No.: US 6,236,049 B1
(45) Date of Patent: May 22, 2001

(54) INFRARED IMAGING OF ULTRASONICALLY EXCITED SUBSURFACE DEFECTS IN MATERIALS

(75) Inventors: Robert L. Thomas; Lawrence D. Favro, both of Huntington Woods; Xiaoyan Han, Plymouth; Zhong Ouyang; Hua Sui, both of Detroit; Gang Sun, Dearborn Heights, all of MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 09/397,585

(22) Filed: Sep. 16, 1999

(51) Int. Cl.[7] .................................................... G01N 29/04
(52) U.S. Cl. ........................................ 250/341.6; 250/334
(58) Field of Search ................................. 250/341.6, 334, 250/338.1, 338.3

(56) References Cited

U.S. PATENT DOCUMENTS

| 3,934,452 | 1/1976 | Prevorsek et al. . | |
| 4,232,554 | 11/1980 | Aleck . | |
| 4,378,701 | 4/1983 | Mountain et al. . | |
| 4,463,608 | * 8/1984 | Takeuchi et al. | 73/606 |
| 4,541,059 | 9/1985 | Toshihiko . | |
| 4,625,557 | * 12/1986 | Rutherford | 73/635 |
| 4,710,030 | * 12/1987 | Tauc et al. | 356/432 |
| 4,828,400 | 5/1989 | Boyce . | |
| 4,878,116 | 10/1989 | Thomas et al. . | |
| 4,950,897 | * 8/1990 | Mandelis et al. | 250/334 |
| 4,950,990 | 8/1990 | Moulder et al. . | |
| 5,201,582 | 4/1993 | Lesniak . | |
| 5,201,841 | 4/1993 | Lebeau et al. . | |
| 5,287,183 | 2/1994 | Thomas et al. . | |
| 5,376,793 | 12/1994 | Lesniak . | |
| 5,417,494 | 5/1995 | Kempa et al. . | |
| 5,476,010 | * 12/1995 | Fleming et al. | 73/620 |
| 5,495,763 | 3/1996 | Rhodes et al. . | |
| 5,748,318 | * 5/1998 | Maris et al. | 356/381 |
| 5,837,896 | 11/1998 | Rhodes et al. . | |

OTHER PUBLICATIONS

"Lockin–thermographie", Institut for Kunststoffprufung und Kunststoffkunde/Abteilung Zerstorungsfreie Prufung, Pfaffenwaldring 32 70 569 Stuttgart.
J. Rantala et al., "Lock–in Thermography with mechanical loss angle heating at ultrasonic frequenices", QIRT 96—Eurotherm Series 50—Edizioni ETS, Pisa 1997, pp. 389–393.
Zhang, Daqing and Sansor, Bela I., ASTM Special Technical Publication, 10th Conf. on Composite Materials: Testing and Design, 1992 ASTM, pp. 428–443.
Mignogna, R.B., Green, Jr, R,E, Duke, Jr., J.C., Henneke, II, E.G., and Reifsnider, K.L., "Thermographic investigation of high–power ultrasonic heating in materials", Ultrasonic, Jul. 1981, pp. 159–165.

* cited by examiner

*Primary Examiner*—Constantine Hannaher
*Assistant Examiner*—Otilia Gabor
(74) *Attorney, Agent, or Firm*—Harness, Dickey & Pierce, P.L.C.

(57) ABSTRACT

A thermal imaging system for detecting cracks and defects in a component. An ultrasonic transducer is coupled to the specimen through a malleable coupler. Ultrasonic energy from the transducer causes the defects to heat up, which is detected by a thermal camera. The ultrasonic energy is in the form of a pulse where the frequency of the ultrasonic signal is substantially constant within the pulse. A control unit is employed to provide timing and control for the operation of the ultrasonic transducer and the camera.

31 Claims, 4 Drawing Sheets

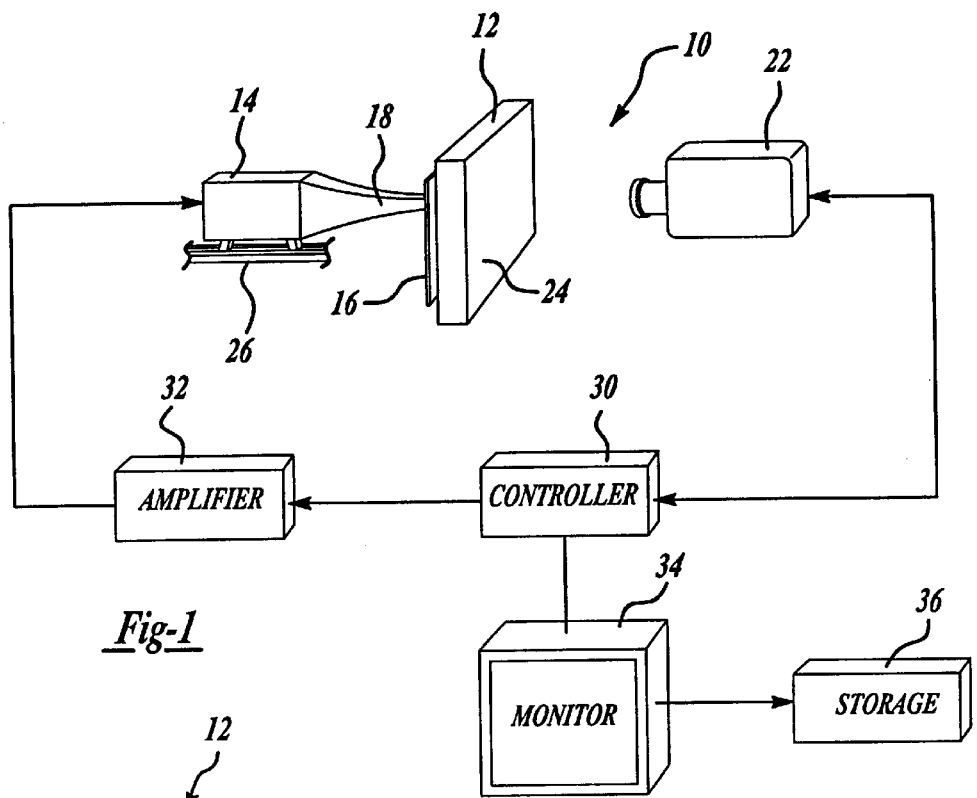
Fig-1
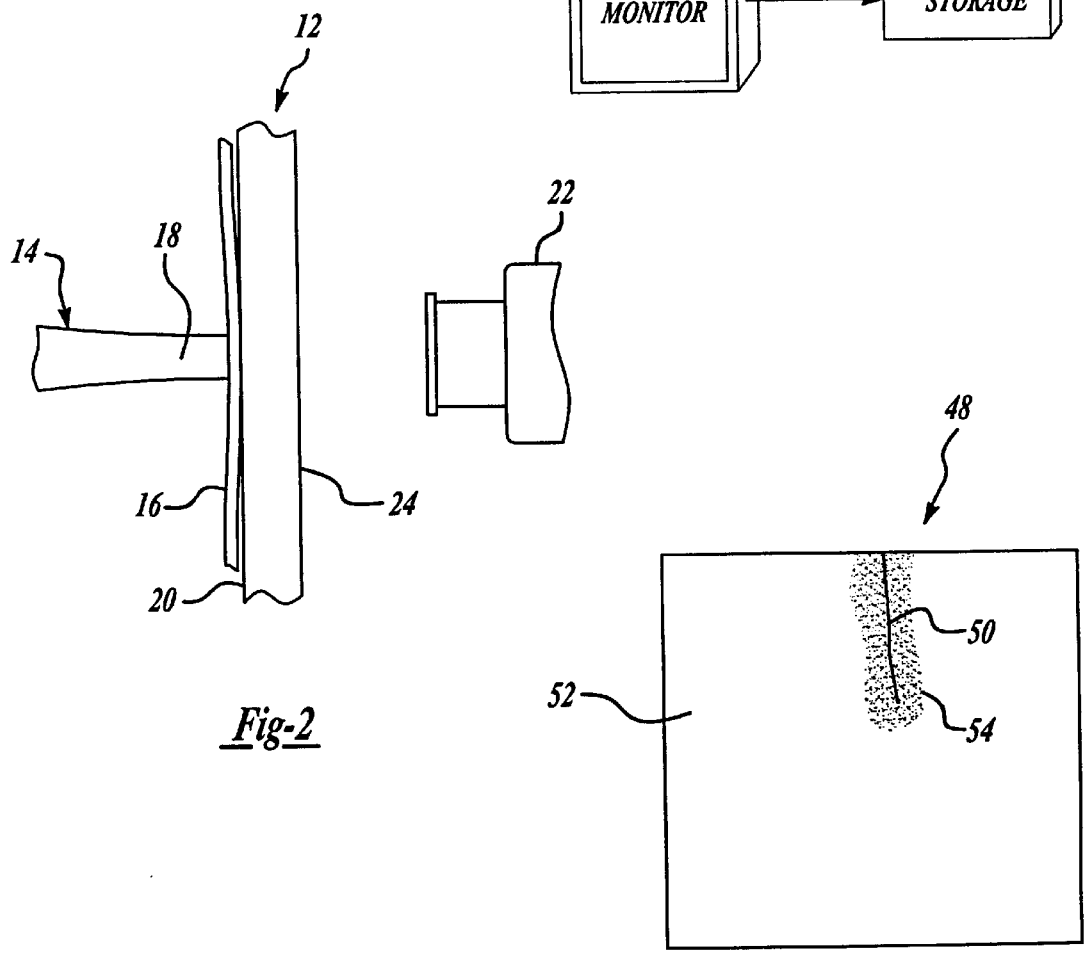
Fig-2
Fig-6

INFRARED IMAGING OF ULTRASONICALLY EXCITED SUBSURFACE DEFECTS IN MATERIALS

BACKGROUND OF THE INVENTION

1. Field of the Invention

This invention relates generally to a system and method for the detection of defects in a material and, more particularly, to a technique for coupling ultrasonic energy into a material to heat cracks and other defects that may exist in the material, and then thermally imaging the material to identify the defects by the heat radiating therefrom.

2. Discussion of the Related Art

Maintaining the structural integrity of certain components and structures is very important in many areas because of safety concerns and the like. Loss of structural integrity is typically caused by material defects, such as cracks, delaminations, disbonds, corrosion, inclusions, voids and the like, that may exist in the component or structure. For example, it is very important in the aviation industry that reliable techniques are available to examine the structural integrity of the aircraft skin and structural components of the aircraft to ensure that the aircraft does not suffer from structural failure when in flight. The structural integrity of turbine blades and rotors, and vehicle cylinder heads is also important in those industries. Therefore, techniques have been developed for the non-invasive and non-destructive analysis of different structural components and materials in various industries.

One known technique for non-invasive and non-destructive testing for material defects includes treating the structural component with a dye penetrant so that the dye enters any crack or defects that may be present in the material. The component is then cleaned, and the structure is treated with a powder that causes the dye remaining in the cracks to wick into the powder. An ultraviolet (UV) light source is used to inspect the material to observe locations on the component that fluoresces as a result of the dye. This technique has the disadvantage, however, that it is highly inspector intensive and dependent because the person inspecting for the fluorescence must be skilled. Additionally, the dye does not typically penetrate tightly closed cracks or cracks that are not on the surface.

A second known technique for inspecting a component for defects employs an electromagnetic coil to induce eddy currents in the component. The coil is moved around on the component, and the eddy current pattern changes at a crack or other defect. The complex impedance in the coil changes as the eddy current changes, which can be observed on an oscilloscope. This technique has the drawback that it is also very operator intensive, and also extremely slow and tedious.

Another known technique employs thermal imaging of the component to identify the defects. Typically, a heat source, such as a flash lamp or a heat gun, is used to direct a planar pulse of heat to the surface of the component. The material of the component absorbs the heat, and emits reflections in the infrared wavelengths. Certain types of defects will cause the surface temperature to cool at a different rate over the defects than for the surrounding areas. A thermal or infrared imaging camera is used to image the component and detect the resulting surface temperature variation. Although this technique has been successful for detecting disbonds and corrosion, it is ordinarily not successful for detecting vertical cracks in the material, that is, those cracks that are perpendicular to the surface. This is because a fatigue crack looks like a knife edge to the planar heat pulse, and therefore no, or minimal, reflections occur from the crack making the cracks hard or impossible to see in the thermal image.

Thermal imaging for detecting defects in a material has been extended to systems that employ ultrasonic excitation of the material to generate the heat. The article Rantala, J. et al, "Lock-in Thermography with Mechanical Loss Angle Heating at Ultrasonic Frequencies," Quantitative Infrared Thermography, Eurotherm Series 50, Edizioni ETS, Pisa 1997, pg 389–393 discloses such a technique. In this technique, ultrasonic excitation is used to cause the crack or defect to "light up" as a result of the ultrasonic field. Particularly, the ultrasonic waves cause the opposing edges of the crack to rub together causing the crack area to heat up. Because the undamaged part of the component is only minimally heated by the ultrasonic waves, the resulting thermal images of the material show the cracks as bright areas against a dark background field.

The transducer used in the ultrasonic thermal imaging technique referred to above makes a mechanical contact with the component being analyzed. However, it is difficult to couple high power ultrasonic energy into some materials, particularly in the case of metals. Significant improvements in this technique can be achieved by improving the coupling between the ultrasonic transducer and the component.

Additionally, the known ultrasonic thermal imaging technique employs complex signal processing, particularly vector lock-in, synchronous imaging. Vector lock-in imaging uses a periodically modulated ultrasonic source and includes a processing technique that synchronously averages successive image frames producing an in-phase image and a quadrature image both based on the periodicity of the source. This results in images that are synchronous with the periodicity and eliminates unsynchronous noise from the image. The periodicity of the image can also be induced by an external stimulus, such as a modulated laser beam, heat lamps, etc. The processor receives the frames of video images and stores them synchronously with the induced periodicity, and then averages the stored frames with subsequently received frames to remove the noise. U.S. Pat. No. 4,878,116 issued Oct. 31, 1989 issued to Thomas et al discloses this type of vector lock-in imaging.

U.S. Pat. No. 5,287,183 issued to Thomas et al Feb. 15, 1994 discloses a synchronous imaging technique that is a modification of the vector lock-in imaging disclosed in the '116 patent. Particularly, the imaging technique disclosed in the '183 patent extends the vector lock-in synchronous imaging technique to include a "box car" technique variation where the source is pulsed, and the images are synchronously averaged at various delay times following each pulse. The box car technique multiplies the video signal by zero except in several narrow time windows, referred to as gates, which are at a fixed time delay from the initiation of each ultrasonic pulse. The effect of these gates is to acquire several images corresponding to the states of component being imaged at the predetermined fixed delay times after the pulses. These different delay times are analogous to the different phases, represented by the sine and cosine functions of the periodic signal in the lock-in technique. During the acquisition of the gated images, the images corresponding to different delay times are combined arithmetically by pixel-by-pixel subtraction to suppress non-synchronous background effects.

The ultrasonic excitation thermal imaging technique has been successful for detecting cracks. However, this technique can be improved upon to detect smaller cracks, as well as tightly closed cracks, with much greater sensitivity. It is therefore an object of the present invention to provide such a defect detection technique.

SUMMARY OF THE INVENTION

In accordance with the teachings of the present invention, a technique is disclosed for infrared or thermal imaging of ultrasonically excited subsurface defects in a material. An ultrasonic source is connected to a specimen being inspected through a coupler that transmits the ultrasonic waves into the material with minimum attenuation. The ultrasonic source emits a single ultrasonic pulse having a constant frequency amplitude for a predetermined period of time. A suitable thermal imaging camera is used to image the specimen when it is being excited by the ultrasonic source. A control unit is used to control the operation of the ultrasonic source and the camera for timing purposes. Although vector lock-in, or box car integration, synchronous imaging techniques can be employed for reducing noise in the images, such signal processing techniques are not required in the present invention.

During initiation of the detection sequence, the control unit instructs the camera to begin taking sequential images of the specimen. Next, the control unit instructs the transducer to emit a pulse of ultrasonic energy at a predetermined frequency for a predetermined time period. A sequence of images are generated that show cracks and other defects in the material as light areas (higher temperature) against a dark (lower temperature) background. The images can be displayed on a monitor, and a storage device can be provided to store the sequence of images to be reviewed at a later time.

Additional objects, advantages and features of the present invention will become apparent from the following description and the appended claims when taken in conjunction with the accompanying drawings.

BRIEF DESCRIPTION OF THE DRAWINGS

FIG. 1 is a block diagram of an imaging system according to the invention;

FIG. 2 is a broken-away, side view of the transducer, specimen and camera of the imaging system shown in FIG. 1;

FIG. 6 is an image generated by the imaging system of the invention, showing a closed crack excited by ultrasonic energy;

DETAILED DESCRIPTION OF THE PREFERRED EMBODIMENTS

Figure 3:
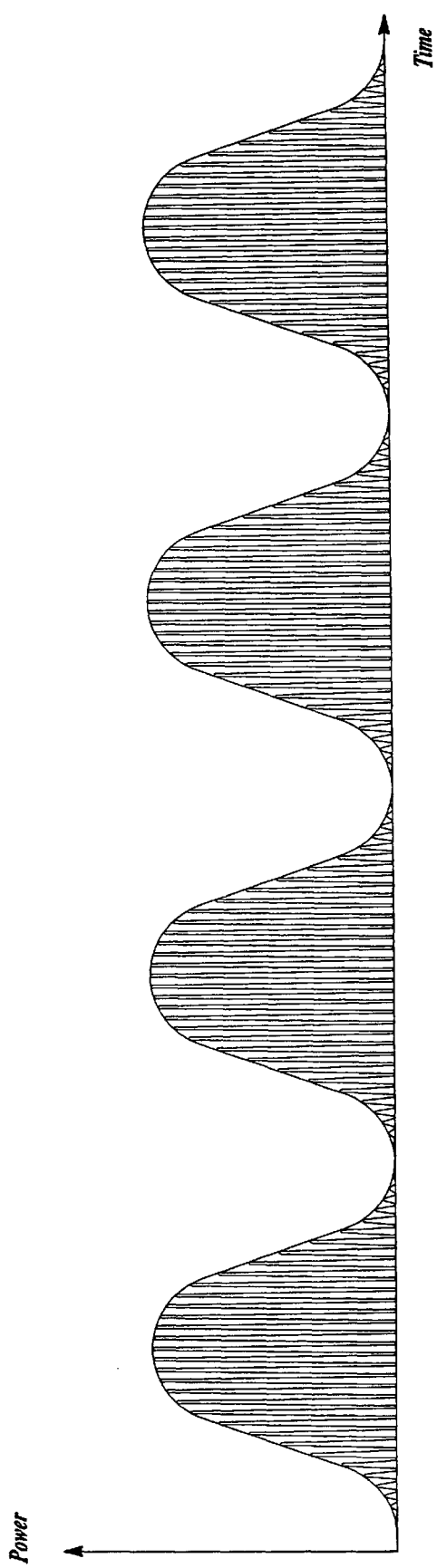
FIG. 3 is a graph with power on the vertical axis and time on the horizontal axis showing the ultrasonic signal used in the known thermal imaging techniques that employ vector lock-in synchronous imaging.

The following description of the preferred embodiments directed to an ultrasonic and thermal imaging system is merely exemplary in nature, and is in no way intended to limit the invention or its applications or uses.

FIG. 1 is a block diagram of an imaging system 10, according to an embodiment of the present invention. The imaging system 10 is being used to detect defects, such as cracks, corrosion, delaminations, disbonds, etc., in a specimen 12. The specimen 12 is intended to represent any structural component or material, such as an aircraft skin, that may include these types of defects. It is stressed that specimen 12 does not need to be metal, but can be other materials, such as ceramics, composites, etc. The system 10 includes an ultrasonic transducer 14 having a piezoelectric element that generates ultrasonic energy within a certain ultrasonic frequency band. The transducer 14 can be any transducer suitable for the purposes described herein, such as the Branson 900 MA ultrasonic transducer. In one embodiment, the ultrasonic transducer 14 generates a pulse of ultrasonic energy having a substantially constant amplitude at a frequency of about 20 kHz for a period of time of about ½ of a second and at a power level of about 1 kW. However, as will be appreciated by those skilled in the art, other ultrasonic frequencies or sonic frequencies, power levels and pulse durations can be used within the scope of the present invention.

The ultrasonic energy from the transducer 14 is coupled to the specimen 12 through a coupler 16. The coupler 16 is in mechanical contact with an end 18 of the transducer 14 and a front side 20 of the specimen 12. FIG. 2 is a broken-away, side view showing the transducer 14 in contact with the coupler 16 and the specimen 12. A support structure 26 is used to help maintain the transducer 14 in contact with the coupler 16. In one embodiment, the coupler 16 is a thin piece of a soft metal, such as copper, to effectively couple the ultrasonic energy into the specimen 12. Of course, other couplers consistent with the discussion herein can be used. The coupler 16 can be any suitable piece of material that is typically softer than the end 18 of the transducer 14, and is malleable to be deformed against the end 18 of the transducer 14 and prevent the transducer 14 from bouncing from or walking along the specimen 12. In one embodiment, the coupler 16 couples about 30 to 40 percent of the ultrasonic energy from the transducer 14 into the specimen 12. It is noted, however, that the coupler 16 may not be needed in certain applications, such as testing for defects in a composite.

A thermal imaging camera 22 is provided and spaced from a back side 24 of the specimen 12, and generates images of the side 24 of the specimen 12 in association with ultrasonic excitations of the specimen 12. The camera 22 can be spaced from the specimen 12 any suitable distance to provide images of as much of the specimen as desired in a single image. In other embodiments, the ultrasonic energy from transducer 14 and the image generated by the camera 22 can be provided at the same side of the specimen 12. The thermal camera 22 can be any camera suitable for the purposes described herein, such as the Galileo camera available from Raytheon. In one embodiment, the camera 22 senses infrared emissions in the 3–5 micron wavelength range, and generates images at 100 frames per second. The camera 22 includes a focal plane array having 256×256 InSb pixels to generate the resolution desirable. In one embodiment, the side 24 of the specimen 12 is painted black to provide better contrast for infrared imaging.

A controller 30 provides timing between the transducer 14 and the camera 22. The controller 30 can be any computer suitable for the purposes described herein. When the detection process is initiated, the controller 30 causes the camera 22 to begin taking sequential images of the specimen 12 at a predetermined rate. Once the sequence of images begins, the controller 30 sends a signal to an amplifier 32 that causes the amplifier 32 to send a pulse to the transducer 14 to generate the pulsed ultrasonic signal. The ultrasonic energy is in the form of a simple pulse at the frequency being used. It is not necessary to employ any type of vector lock-in or synchronous imaging techniques between the pulse of energy and the imaging, as is currently done in the prior art. However, such signal processing techniques can be used to further reduce noise. It is stressed that the frequencies and pulse time periods being described herein are by way of non-limiting examples, in that different frequencies, pulse times, input power, etc. will vary from system to system and specimen being tested. After the end of the pulse, the controller 30 instructs the camera 22 to stop taking images. The images generated by the camera 22 are sent to a monitor 34 that displays the images of the side 24 of the specimen 12. The images can then be sent to a storage device 36 to be viewed at another location if desirable.

The ultrasonic energy applied to the specimen 12 causes faces of the defects and cracks in the specimen 12 to rub against each other and create heat. This heat appears as bright spots in the images generated by the camera 22. Therefore, the system is very good at identifying very small tightly closed cracks. For those cracks that may be open, where the faces of the crack do not touch, the heating is generated at the stress concentration point at the crack tip. This point appears as a bright spot on the images indicating the end or tip of an open crack. The ultrasonic energy is effective to heat the crack or defect in the specimen 12 no matter what the orientation of the crack is relative to the energy pulse. The camera 22 takes an image of the surface 24 of the specimen 12, providing a visual indication of any crack in the specimen 12 no matter what the position of the crack within the thickness of the specimen 12.

The present invention provides improvements over the known ultrasonic and thermal imaging techniques because the ultrasonic pulses used to heat the cracks and defects are simple pulses having a substantially constant amplitude, and do not need to employ sinusoidal signal modulation as used in vector lock-in synchronous imaging. To illustrate this point, FIG. 3 shows a graph with power on the vertical axis and time on the horizontal axis depicting the waveform of the ultrasonic signal used in vector lock-in imaging. The ultrasonic signal is generated at a predetermined frequency, and modulated with a low frequency sinusoidal modulating wave that provides amplitude modulation at a predetermined modulation period. The ultrasonic frequency signal rises and falls in amplitude with the low frequency modulation wave. Typically, the ultrasonic excitation is performed over several seconds. The image generated by this imaging technique is not the actual image of the particular component being imaged, but is a difference image generated by the subtraction process of the synchronous imaging. A more detailed discussion of this type of vector lock-in synchronous imaging to reduce noise in these types of systems is discussed in the '116 patent.

Figure 4:
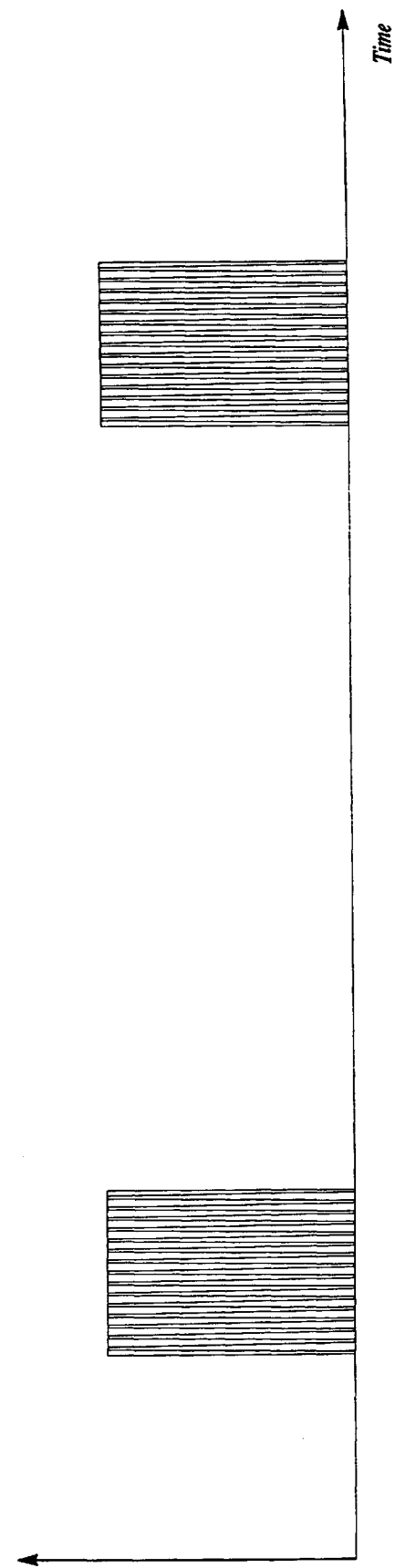
FIG. 4 is a graph with power on the vertical axis and time on the horizontal axis showing the pulsed ultrasonic signal used in the thermal imaging technique of the present invention.

FIG. 4 is a graph with power on the vertical axis and time on the horizontal axis showing the pulses used to provide the ultrasonic excitation in the present invention. The ultrasonic frequency signal within each pulse has substantially the same amplitude, and is not modulated by a lower frequency sinusoidal waveform. The images generated by the camera 22 are real images, and not difference images of the type generated in the vector lock-in synchronous imaging technique. This provides a significant improvement in image quality and control simplicity. Although one pulse is ordinarily sufficient, more than one pulse can be employed, separated in time by a predetermined time period, for signal averaging purposes to reduce noise. The technique of "box car" integration can be used as discussed in the '183 patent. In this technique, a gate is used in each time window to identify an image for each pulse, where the gate is at a certain fixed time delay from the beginning of the pulse. During the acquisition of the gated images, the images corresponding to different delay times are combined arithmetically to suppress non-synchronous background effects.

Figure 5A:
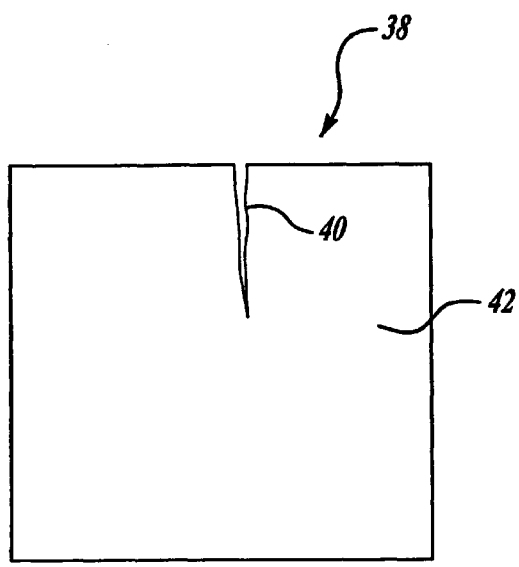
FIGS. 5(a)–5(d) show consecutive images at predetermined time intervals of an open crack in a specimen that has been ultrasonically excited and imaged by an imaging system of the present invention.
Figure 5B:
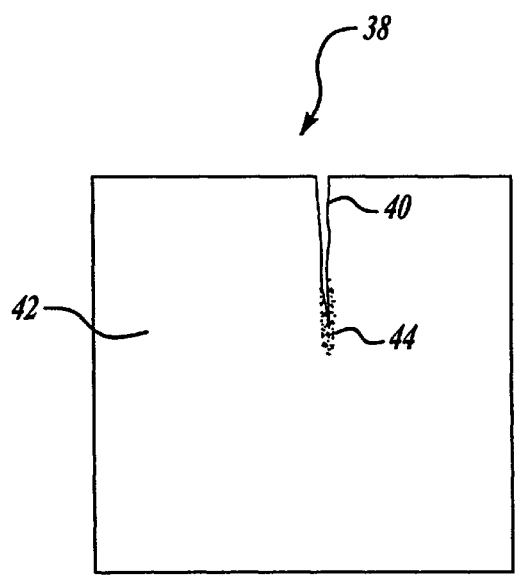
Figure 5C:
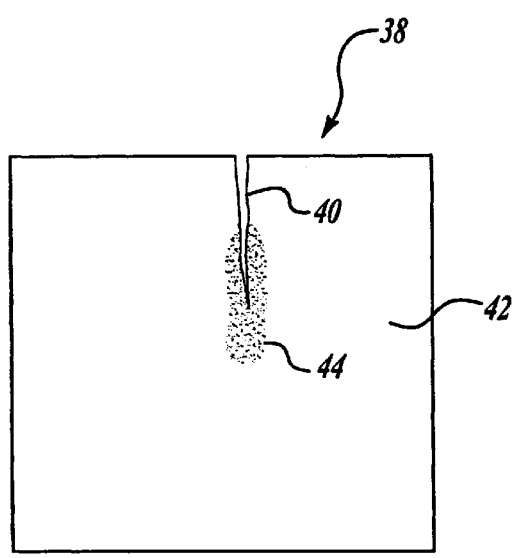
Figure 5D:
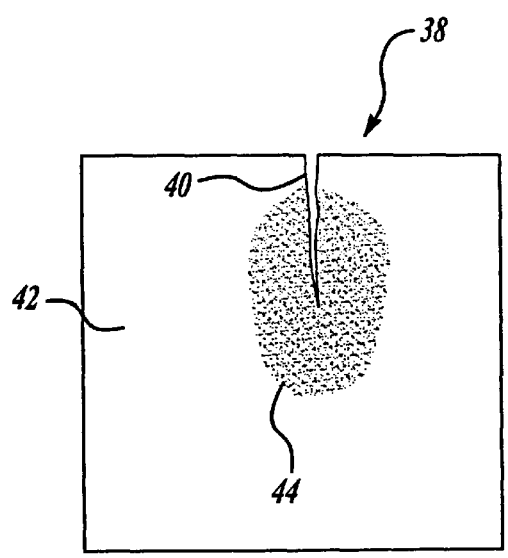

FIGS. 5(a)–5(d) show four sequential images 38 of an open fatigue crack 40 in a metal specimen 42. FIG. 5(a) shows the images 38 of the specimen 42 prior to the ultrasonic energy being applied. FIG. 5(b) shows the image 38 of the specimen 42 14 ms after the ultrasonic energy is applied. As is apparent, a light (higher temperature) spot 44 (sketched as a dark region) appears at the closed end of the crack 40, where the mechanical agitation causes the heating. FIGS. 5(c) and 5(d) show subsequent images 38 at time equal to 64 ms and time equal to 114 ms, respectively. The light spot 44 on the specimen 42 increases dramatically over this sequence, clearly indicating the location of the crack 40.

FIG. 6 shows an image 48 of a closed crack 50 in a specimen 52 after being energized by the ultrasonic pulse. In this embodiment, because the crack 50 is closed, the entire length of the crack 50 generates heat creating a light spot 54 along the entire length of the crack 50 and providing an indication of a closed crack. Because the ultrasonic energy is so effective in causing the closed crack 50 to heat up significantly relative to the background, very short closed cracks, for example on the order of ⅔ mm, are readily ascertainable in the image 48.

Figure 7:
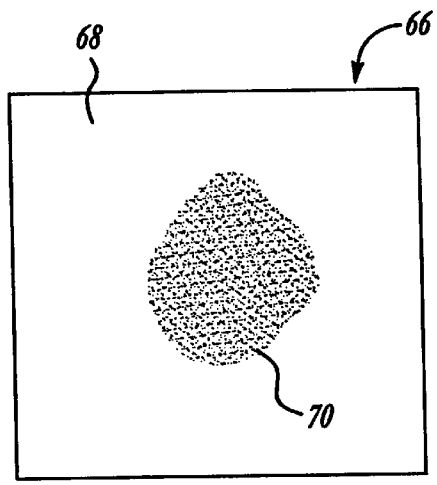
FIG. 7 is an image generated by the imaging system of the present invention, showing a delamination or disbond excited by the ultrasonic energy.

FIG. 7 shows an image 66 of a specimen 68. In this image, a light spot 70 is shown, and is intended to represent the type of image generated from the thermal energy that is created by ultrasonically exciting a delamination or disbond. The thermal imaging technique of the present invention is particularly useful in identifying "kissing" disbonds.

Figure 8:
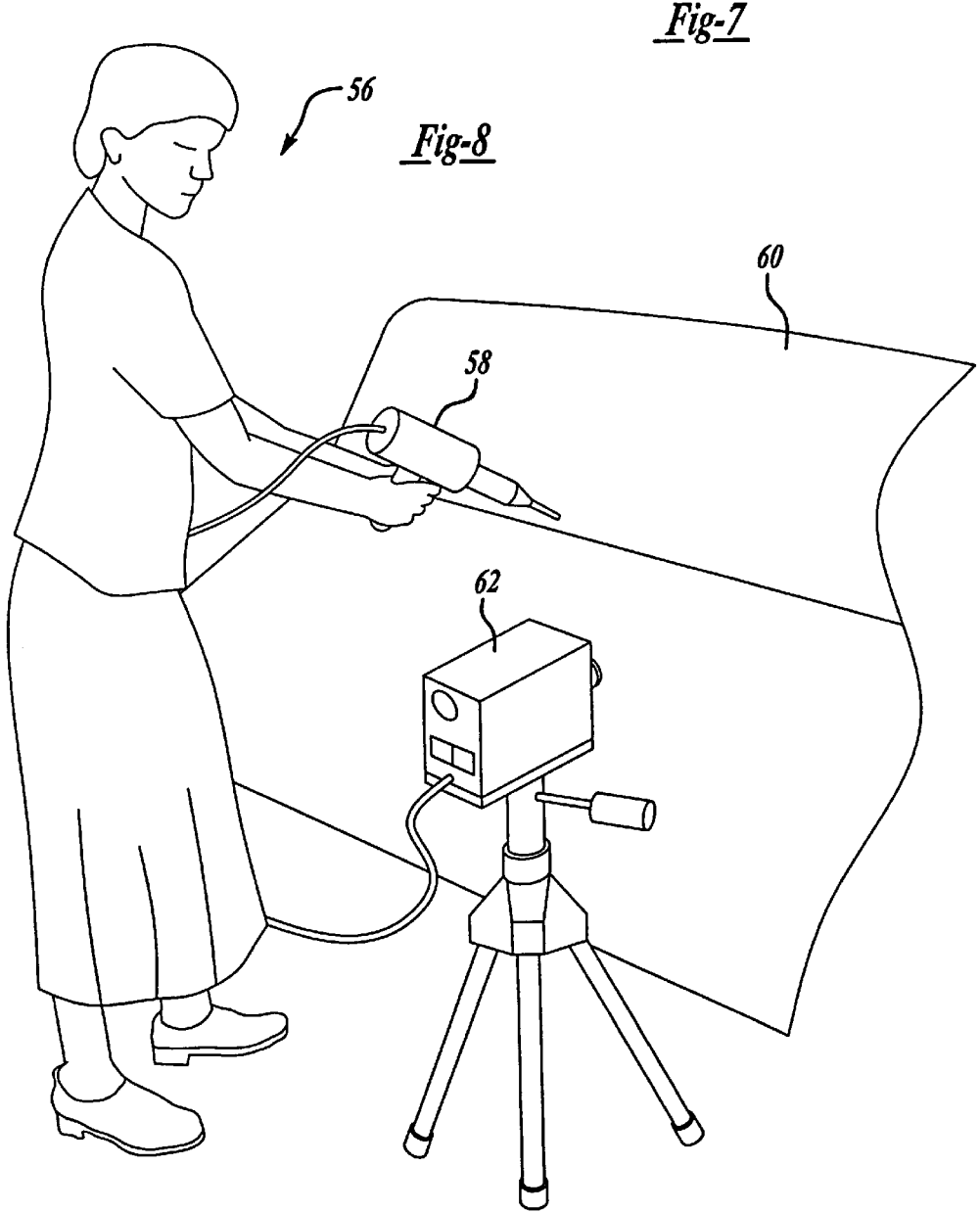
FIG. 8 is a perspective view of a person holding an ultrasonic transducer against an aircraft component, and using the imaging system of the present invention to detect cracks in the component.

FIG. 8 is a perspective view of an operator 56 holding a hand-held transducer 58 against a specimen 60, such as an aircraft fuselage. A thermal imaging camera 62 is directed towards the specimen 60 at a location that is separate from the point of contact of the transducer 58. FIG. 8 illustrates that the system according to the invention can be used in the field for testing such components.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A thermal imaging system for detecting defects in a component, said system comprising:

a sound source;

a thermal imaging camera directed towards the component and generating thermal images of the component; and a controller electrically connected to the sound source and the camera, said controller causing the sound source to emit at least one pulse of a sound signal at a predetermined frequency and for a predetermined duration, and causing the camera to generate sequential images of the component, wherein the frequency of the sound signal has a substantially constant amplitude, and wherein vibrational energy from the sound source causes the defects in the component to heat up and be visible in the images generated by the camera.

2. The system according to claim 1 wherein the at least one pulse is a plurality of pulses separated by a predetermined time, and wherein the controller averages images taken within a predetermined window in each pulse, where the window is provided at the same delay time in each pulse from when the pulse is initiated.

3. The system according to claim 1 wherein the at least one pulse is a series of pulses, and wherein the system employs a box car integration technique to provide signal averaging of the images.

4. The system according to claim 1 wherein the sound source emits the pulse for a duration of one-half of a second or less.

5. The system according to claim 1 further comprising a coupler positioned between and in contact with the component and the sound source.

6. The system according to claim 5 wherein the coupler is malleable and is softer than an end of the sound source in contact with the coupler.

7. The system according to claim 5 wherein the coupler is a thin piece of metal.

8. The system according to claim 7 wherein the coupler is a copper member.

9. The system according to claim 1 further comprising a monitor responsive to the images from the camera, said monitor displaying the images.

10. The system according to claim 1 wherein the camera is directed towards the component at a location that is separate from the location where the sound source contacts the component.

11. A defect detection system for detecting defects in a structure, said system comprising:
    a sound source for directing at least one pulse of a sound signal into the structure for a predetermined period of time, said signal having a predetermined frequency and a substantially constant amplitude;
    a camera directed towards the structure and generating images of the structure when the source emits the sound signal; and
    a controller connected to the source and the camera to provide timing signals therebetween, said controller being responsive to the images from the camera.

12. The system according to claim 11 wherein the at least one pulse is a plurality of pulses separated by a predetermined time, and wherein the system averages images taken within a predetermined window in each pulse, where the window is provided at the same delay time in each pulse from when the pulse is initiated.

13. The system according to claim 11 wherein the at least one pulse is a series of pulses, and wherein the system employs a box car integration technique to provide signal averaging of the images.

14. The system according to claim 11 wherein the sound source emits the pulse for a duration of one-half of a second or less.

15. The system according to claim 11 further comprising a coupler positioned in contact with the structure and the source, said coupler being a malleable member.

16. The system according to claim 15 wherein the coupler is a thin piece of metal.

17. The system according to claim 11 wherein the controller causes the camera to take sequential images of the structure before, during and after when the sound source emits the sound signal.

18. The system according to claim 11 wherein the camera is directed towards the structure at a location that is separate from a location where the source contacts the structure.

19. A method of detecting defects in a structure, said method comprising the steps of:
    emitting at least one pulse of a sound signal into the structure to heat the defects, said signal having a predetermined frequency and a substantially constant amplitude; and
    generating a sequence of thermal images of the structure prior to, during and after the emission of the sound signal.

20. The method according to claim 19 further comprising the steps of emitting a plurality of pulses of the sound signal, and providing signal averaging of images generated in a window in each separate pulse where the window is provided at the same delay time in each pulse from when the pulse is initiated.

21. The method according to claim 19 further comprising the step of processing the images using a box car synchronous imaging technique.

22. The method according to claim 19 wherein the step of emitting a pulse of the sound signal includes emitting the pulse for a duration of one-half of a second or less.

23. The method according to claim 19 further comprising the step of providing a coupler in contact with the structure and in contact with a sound source that generates the sound signal.

24. The method according to claim 23 wherein the step of providing a coupler includes providing a coupler that is malleable and conforms to an end of the sound source in contact with the structure.

25. The system according to claim 1 wherein the sound source is an ultrasonic transducer and the at least one pulse is an ultrasonic pulse.

26. The system according to claim 11 wherein the sound source is an ultrasonic source and the sound signal is an ultrasonic signal.

27. The method according to claim 19 wherein the step of emitting at least one pulse includes emitting at least one pulse of ultrasonic energy.

28. A defect detection system for detecting defects in a structure, said system comprising:
    a sound source;
    a coupler positioned between and in contact with the structure and the sound source;
    a thermal imaging camera directed towards the structure, and generating thermal images of the structure; and
    a controller electrically coupled to the sound source and the camera, said controller causing the sound source to emit a sound signal at a predetermined frequency for a predetermined duration, the signal having a substantially constant amplituide, and causing the camera to generate sequential images of the structure, wherein the sound signal from the sound source causes the defects in the structure to heat up and be visible in the images generated by the camera.
    The limitation that the sound signal has a substantially constant amplitude was necessary to overcome any application of the prior art.

29. The system according to claim 28 wherein the coupler is malleable and is softer than an end of the sound source.

30. The system according to claim 29 wherein the coupler is a thin piece of metal.

31. The system according to claim 30 wherein the coupler is a copper member.

* * * * *

UNITED STATES PATENT AND TRADEMARK OFFICE
CERTIFICATE OF CORRECTION

PATENT NO. : 6,236,049 B1
DATED : May 22, 2001
INVENTOR(S) : Robert L. Thomas, Lawrence D. Favro, Xiaoyan Han, Zhong Ouyang, Hua Sui and Gang Sun Page 1 of 1

It is certified that error appears in the above-identified patent and that said Letters Patent is hereby corrected as shown below:

Column 8,
Line 45, "amplituide" should be -- amplitude --.

Signed and Sealed this

Fifteenth Day of January, 2002

Attest:

JAMES E. ROGAN
Director of the United States Patent and Trademark Office

Attesting Officer

UNITED STATES PATENT AND TRADEMARK OFFICE
CERTIFICATE OF CORRECTION

PATENT NO. : 6,236,049 B1
DATED : May 22, 2001
INVENTOR(S) : Thomas et al.

It is certified that error appears in the above-identified patent and that said Letters Patent is hereby corrected as shown below:

Column 8,
Lines 50-52, delete "The limitation that the sound has a substantially constant amplitude was necessary to overcome any application of the prior art. --

Signed and Sealed this

Eleventh Day of November, 2003

JAMES E. ROGAN
*Director of the United States Patent and Trademark Office*